United States Patent
Chen et al.

(10) Patent No.: US 9,114,089 B2
(45) Date of Patent: *Aug. 25, 2015

(54) MODULATION OF THYMOSIN BETA-4 IN SKIN

(71) Applicant: Avon Products, Inc., Suffern, NY (US)

(72) Inventors: Siming W. Chen, Basking Ridge, NJ (US); Qian Zheng, Morris Plains, NJ (US); Satish Parimoo, Bridgewater, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/100,514

(22) Filed: Dec. 9, 2013

(65) Prior Publication Data

US 2014/0154343 A1 Jun. 5, 2014

Related U.S. Application Data

(63) Continuation of application No. 13/324,150, filed on Dec. 13, 2011, now Pat. No. 8,632,827.

(51) Int. Cl.

| | |
|---|---|
| *A01N 65/00* | (2009.01) |
| *A61K 8/44* | (2006.01) |
| *A61K 36/00* | (2006.01) |
| *A61Q 19/08* | (2006.01) |
| *A61K 8/97* | (2006.01) |
| *C12Q 1/68* | (2006.01) |
| *A61K 8/49* | (2006.01) |
| *A61Q 19/00* | (2006.01) |
| *A61Q 19/02* | (2006.01) |
| *A61Q 19/06* | (2006.01) |

(52) U.S. Cl.
CPC . *A61K 8/44* (2013.01); *A61K 8/445* (2013.01); *A61K 8/49* (2013.01); *A61K 8/494* (2013.01); *A61K 8/4926* (2013.01); *A61K 8/97* (2013.01); *A61K 36/00* (2013.01); *A61Q 19/00* (2013.01); *A61Q 19/02* (2013.01); *A61Q 19/06* (2013.01); *A61Q 19/08* (2013.01); *C12Q 1/68* (2013.01)

(58) Field of Classification Search
CPC ....................................... A61K 36/00
USPC ........................................ 424/725
See application file for complete search history.

(56) References Cited

U.S. PATENT DOCUMENTS

| | | | |
|---|---|---|---|
| 5,869,540 | A | 2/1999 | Smith |
| 7,101,663 | B2 | 9/2006 | Godfrey et al. |
| 7,662,561 | B2 | 2/2010 | Godfrey et al. |
| 8,455,518 | B2 | 6/2013 | Khusial et al. |
| 2004/0067227 | A1 | 4/2004 | Goldstein |
| 2004/0197429 | A1 | 10/2004 | Obukowicz et al. |
| 2005/0154046 | A1 | 7/2005 | Wang et al. |
| 2006/0292572 | A1 | 12/2006 | Stuart et al. |
| 2011/0014149 | A1 | 1/2011 | Park et al. |
| 2011/0111010 | A1 | 5/2011 | Touitou |
| 2011/0151031 | A1 | 6/2011 | Futamura |
| 2011/0177970 | A1 | 7/2011 | Chauchereau et al. |
| 2011/0206793 | A1 | 8/2011 | Hines et al. |
| 2011/0236325 | A1 | 9/2011 | Mitchel et al. |
| 2013/0149268 | A1 | 6/2013 | Chen et al. |

OTHER PUBLICATIONS

"Flora of China" FOC vol. 15 p. 7. No. 20 Maesa japonica http://web.archive.org/web/20060227034028/http://www.efloras.org/florataon.aspx?flora_id=2&taxon-id=200016854. Feb. 27, 2006.

Rai "Medicinal Plants of Tehrathum District, Eastern Nepal" Our Nature (2003) 1:42-48 p. 46 item 59.

Biflora database of platns "Maesa japonica" http://biflora.org/abc_sea/m_plants/plant01m/images.html. Sep. 5, 2008.

Girardi, M., et al., Immunology, 2003, 109: 1-7.

Young, JD. et al., Thymosin beta 4 sulfoxide is an anti-inflammatory agent generated by monocytes in the presence of glucocorticoids, Nature Medicine, Dec. 1999; 5(12):1424-7.

Philip D., Animal studies with thymosin beta, a multifunctional tissue repair and regeneration peptide. Ann NY Acad Sci, Apr. 2010; 1194:81-6.

Malinda, K. et al., Thymosin B4 Accelerates Wound Healing, J Invest Dermatol, 1999, 113:364-368.

Bernard, F. et al., Comparison of gene expression profiles in human keratinocyte mono-layer cultures, reconstituted epidermis and normal human skin; transcriptional effects of retinoid treatments in reconstituted human epidermis, Experimental Dermatology 2002: 11:59-74.

G. Costin and V. Hearing, "Human skin pigmentation: melanocytes modulate skin color in response to stress," The FASEB Journal vol. 21, pp. 976-994, Apr. 2007.

Lodish, et al. Molecular Cell Biology, W.H. Freeman, New York, NY 4th edition, 2000.

Lodish, et al. Molecular Cell Biology, W.H. Freeman New York, NY 4th edition, 2000.

*Primary Examiner* — Michael Meller

(74) *Attorney, Agent, or Firm* — David M. Joyal; Joan M. McGillycuddy

(57) ABSTRACT

Methods for preventing, ameliorating, or reducing dermatological signs of aging are provided which employ active agents, other than a retinoid, that stimulate thymosin beta-4 expression in the skin. Also provided are methods for screening for substances which stimulate thymosin beta-4 expression levels and the methods of using active agents identified by the screening protocol in the treatment of skin.

6 Claims, No Drawings

SEQUENCE LISTING

<160> NUMBER OF SEQ ID NOS: 4

<210> SEQ ID NO 1
<211> LENGTH: 44
<212> TYPE: PRT
<213> ORGANISM: Homo sapiens

<400> SEQUENCE: 1

Met Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
        35                  40

<210> SEQ ID NO 2
<211> LENGTH: 657
<212> TYPE: DNA
<213> ORGANISM: Homo sapiens

<400> SEQUENCE: 2

```
gacaactcgg tggtggccac tgcgcagacc agacttcgct cgtactcgtg cgcctcgctt      60
cgcttttcct ccgcaaccat gtctgacaaa cccgatatgg ctgagatcga gaaattcgat     120
aagtcgaaac tgaagaagac agagacgcaa gagaaaaatc cactgccttc caaagaaacg     180
attgaacagg agaagcaagc aggcgaatcg taatgaggcg tgcgccgcca atatgcactg     240
tacattccac aagcattgcc ttcttatttt acttctttta gctgtttaac tttgtaagat     300
gcaaagaggt tggatcaagt ttaaatgact gtgctgcccc tttcacatca aagaactact     360
gacaacgaag gccgcgcctg cctttcccat ctgtctatct atctggctgg cagggaagga     420
aagaacttgc atgttggtga aggaagaagt ggggtggaag aagtggggtg ggacgacagt     480
gaaatctaga gtaaaaccaa gctggcccaa ggtgtcctgc aggctgtaat gcagtttaat     540
cagagtgcca ttttttttt tgttcaaatg attttaatta ttggaatgca caattttttt     600
aatatgcaaa taaaagttt aaaaacttaa aaaaaaaaa aaaaaaaaa aaaaaaa         657
```

<210> SEQ ID NO 3
<211> LENGTH: 44
<212> TYPE: PRT
<213> ORGANISM: Mus musculus

<400> SEQUENCE: 3

Met Ser Asp Lys Pro Asp Met Ala Glu Ile Glu Lys Phe Asp Lys Ser
1               5                   10                  15

```
Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
            35                  40

<210> SEQ ID NO 4
<211> LENGTH: 670
<212> TYPE: DNA
<213> ORGANISM: Mus musculus

<400> SEQUENCE: 4
atcacctcat ttgcatagaa gcacacataa agcggcgttc gccgcgcccc tcccgacaat      60
ccgcagcggc ttctgagcag atcagactct cctcgttcgc gcagctcgct cggctccttc    120
cagcaaccat gtctgacaaa cccgatatgg ctgagatcga gaattcgat aagtcgaagt     180 tgaagaaaac agaaacgcaa gagaaaaatc ctctgccttc aaaagaaaca attgaacaag    240
agaagcaagc tggcgaatcg taatgaggcg agccgcca atatgcactg tacattccac     300
gagcattgcc ttcttatttt acttcttta gctgtttaac tttgtaagat gcaaagaggt    360
tggatcaagt ttaaatgact gtgctgcccc tttcacatca aagaatcaga actactgagc    420
aggaaggcct cccctgcctc tcccacccat ctgatggtct ggctagcaga gagggaaaag    480
aacttgcatg ttggtgaagg aaaaagctgg gtgggagatg atgaaataga gaggaaaatt    540
caagatggtc aaagatgtcc tgcaggatgt aaaatgcagt ttaatcagag tgccattttt    600
ttttgttcaa acaattttaa ttattggaat gcacaatttt tttaatatgc aaataaagtt    660
ttaaaacctg                                                           670
```

MODULATION OF THYMOSIN BETA-4 IN SKIN

CROSS-REFERENCE TO RELATED APPLICATIONS

This patent application is a continuation of, and claims priority to, U.S. patent application Ser. No. 13/324,150, filed on Dec. 13, 2011. The entirety of the aforementioned application is incorporated herein in its entirety by reference.

SEQUENCE LISTING

The instant application contains a Sequence Listing which has been submitted in ASCII format via EFS-Web and is hereby incorporated by reference in its entirety. Said ASCII copy, created on Dec. 4, 2013, is named SC132U1-US sequence listing statement.txt and is 3,063 bytes in size.

FIELD OF INVENTION

The present invention relates generally to methods of improving the aesthetic appearance and health of human skin and also to methods for identifying compounds useful for treating skin. In particular, the invention relates to compounds, other than retinoids, that stimulate thymosin beta-4 expression in skin.

BACKGROUND

Thymosins refer to a family of biochemically and functionally distinct proteins that were originally identified from the thymus, but which are now known to be present in many other tissues, and which have a variety of different physiological functions. More than 20 isoforms of beta-thymosin have been identified in different species, and among humans, three beta-thymosins have been identified, including thymosin beta-4, thymosin beta-10, and thymosin beta-15, all of which share significant amino acid sequence homology. Despite this homology, each of these thymosin beta proteins is a distinct gene product with different functions.

Thymosin beta-4, the most abundant of the beta-thymosins, is a highly conserved, water-soluble amino acid acidic polypeptide. The mammalian gene encoding thymosin beta-4 localizes to the X-chromosome. Human thymosin beta-4, X-linked, has 44 amino acids (msdkpdmaei ekfdksklkk tetqeknplp sketieqekq ages, SEQ ID NO:1), and escapes X-inactivation by being processed into a 43 amino acid peptide, with a molecular weight of 4.9 kDa, by removal of the first methionyl residue (Girardi, M., et al., *Immunology*, 2003, 109: 1-7). Thymosin beta-4 is localized to both the cytoplasm and the nucleus of cells. Thymosin beta-4 is present in many tissues, and has multiple biological functions. It potently regulates actin polymerization, stimulates tissue remodeling, cell differentiation, and cell and tissue healing after injury, and is also involved in the expression of a number of inflammatory chemokines and cytokines.

The inventors have examined the mode of operation of retinol in human skin, and have made the discovery that retinol is a potent upregulator of thymosin beta-4. This surprising result lead to the search for additional agents that upregulate thymosin beta-4, that could act as potential alternatives or replacements for retinol in the treatment of and in the improvement of the aesthetic appearance and health of human skin.

It is an object of the invention to provide compositions and methods for treating, ameliorating, inhibiting and/or preventing dermatological signs of aging. It is another object of the invention to provide methods for treating, ameliorating, inhibiting and/or preventing dermatological signs of aging by inducing the expression of thymosin beta-4 in skin cells to improve the appearance of skin. It is a further object of the invention to provide compounds, other than retinoids, that stimulate thymosin beta-4 expression, for a time sufficient to improve the aesthetic appearance of said human skin, and to provide methods for identifying compounds that are useful for treating, ameliorating, inhibiting and/or preventing dermatological signs of aging, by administering agents that stimulate or upregulate expression of thymosin beta-4 in skin cells.

The foregoing discussion is presented solely to provide a better understanding of nature of the problems confronting the art and should not be construed in any way as an admission as to prior art.

SUMMARY OF THE INVENTION

In accordance with the foregoing objectives and others, the present invention provides stimulators, other than retinoids, of thymosin beta-4, to improve one or more signs of dermatological aging. The stimulators upregulate levels of thymosin beta-4 in the skin. It is believed that upregulators of thymosin beta-4 within dermal fibroblasts and epidermal keratinocytes lead to increased protein production within the cells, including, for example, the fibroblast specific proteins, collagen, elastin, and fibrillin, and the keratinocyte protein keratin. Given the importance of fibroblast-produced proteins to overall skin strength and health, upregulation of thymosin beta-4 will have a beneficial effect on reducing the appearance of aging on skin.

In one aspect of the invention, a method is provided for improving the aesthetic appearance of human skin comprising topically applying to an area of the skin in need thereof using an effective amount of an active agent, other than a retinoid, that stimulates thymosin beta-4 expression, for a time sufficient to improve the aesthetic appearance of said human skin. The sufficiency of the time will be determined by individual response, in particular where wrinkles and/or fine lines are treated, but encompasses once daily administration for from one to four weeks.

In another aspect of the invention, a method is provided for screening candidate substances to identify actives useful for improving the aesthetic appearance of skin. The method comprises assaying candidate substances for ability to stimulate thymosin beta-4 expression in a dermal fibroblast or keratinocyte. The method typically involves incubating human dermal fibroblasts or keratinocyte with a candidate substance and subsequently measuring the levels of mRNA encoding thymosin beta-4 by a quantitative technique such as quantitative polymerase chain reaction (qPCR). The cell used in the assay may be any animal cell that expresses thymosin beta-4, but is preferably mammalian, and is more preferably a human or mouse cell.

Methods are also provided for improving the aesthetic appearance of human skin comprising topically applying to an area of the skin in need thereof an effective amount of a substance that stimulates thymosin beta-4 levels in human skin cells, for example in dermal fibroblasts and epidermal keratinocytes. The thymosin beta-4 stimulators are referred to herein as "actives" or upregulators, and typically will be formulated in a cosmetically acceptable vehicle and topically applied to a human integument, such as the skin of the face, neck, hands, chest, legs, etc., for a time sufficient to enhance the health or aesthetic appearance thereof.

In one aspect of the invention, a method is provided for improving the aesthetic appearance of human skin comprising topically applying to an area of the skin in need thereof an effective amount of an active agent that stimulates (e.g., upregulates) cellular levels of thymosin beta-4, wherein the ability of the active agent to stimulate thymosin beta-4 has been determined by an assay which measures the expression level of thymosin beta-4 in a cell that has been contacted with the active agent. The cell used in the assay may be any animal cell that expresses thymosin beta-4, but is preferably mammalian, and is more preferably a human or mouse cell. The cell may be a skin cell, such as a fibroblast or keratinocyte. The assay may measure the levels of any homolog, fragment or marker of thymosin beta-4, but typically what is measured are the expression levels of thymosin beta-4, which is expressed by the human gene TMSB4X or by the mammalian gene tmsb4x. The expression levels of the human gene TMSB4X or the mouse gene tmsb4x may be determined, for example, by measuring the expression levels of the corresponding mRNA by any suitable technique, such as quantitative polymerase chain reaction (qPCR).

As used herein, the term "thymosin beta-4" refers to a protein, such as the proteins encoded in humans by the TMSB4X gene and in mammals such as mice by the tmsb4x gene. The thymosin beta-4 protein (and its associated RNA and/or DNA encoding thymosin beta-4) as described in the present invention may be from any animal, but is typically human or mouse thymosin beta-4, and preferably human thymosin beta-4. The nomenclature used herein to describe specific thymosin beta-4 examples is that of the National Center for Biotechnology Information ("NCBI"), Accession Numbers NP_066932 (human, thymosin beta-4, protein), NM_021109 (human, thymosin beta-4, mRNA), NP_067253 (mouse, thymosin beta-4, protein), NM_021278 (mouse, thymosin beta-4, mRNA), which are hereby incorporated by reference and summarized in Table 1.

Methods are also provided for treating a skin condition comprising topically applying to an area of the skin in need thereof an effective amount of an active agent that upregulates thymosin beta-4, wherein the ability of said active agent to stimulate the thymosin beta-4 expression has been determined by an assay which measures the expression level of thymosin beta-4 in a cell that has been contacted with said active agent.

A method of treating wrinkles and/or fines lines is also provided, comprising topically applying to an area of the skin in need thereof an effective amount of an active agent that upregulates thymosin beta-4, wherein the ability of the active agent to upregulate thymosin beta-4 has been determined by an assay which measures the expression level of thymosin beta-4 in a cell that has been contacted with the active agent. The assaying step most typically comprises incubating human dermal fibroblasts with a candidate substance and subsequently measuring the levels of mRNA encoding thymosin beta-4, wherein the candidate substance was selected for use as an active agent, in part, on the basis of its ability to upregulate thymosin beta-4 expression. The cell used in the assay may be any animal cell that expresses thymosin beta-4, but is preferably mammalian, and is more preferably a human or mouse cell.

In another aspect of the invention, a cosmetic composition is provided for improving the aesthetic appearance of human skin comprising a cosmetically acceptable vehicle in the form of a water-in-oil or oil-in-water emulsion, and an effective amount of an active agent, other than a retinoid, that upregulates thymosin beta-4.

In yet another aspect of the invention, compositions are provided comprising an amount of a botanical extract effective to upregulate thymosin beta-4 in a dermal fibroblast or keratinocyte, and a cosmetically acceptable vehicle, wherein said botanical extract is extracted from a plant selected from the group consisting of *Maesa japonica, Celosia argentea, Berchemia lineata, Ixora chinesis, Physalis minima*, and combinations thereof.

Further aspects, features and advantages of the present invention will be better appreciated upon a reading of the detailed description of the invention.

DETAILED DESCRIPTION OF THE INVENTION

All terms used herein are intended to have their ordinary meaning unless otherwise provided. By "cosmetically acceptable," it is meant that a particular component is generally regarding as safe and non-toxic at the levels employed. The term "prevent," as used herein, includes delaying the onset or progression of a particular sign of skin aging. The term "thin skin" includes skin that becomes thinner with chronological aging as well as prematurely thinned skin, which may be caused, for example, by photo-aging. The phrase "individual in need thereof" refers to a human that could benefit from improved dermal appearance or health, including males or females. The term "skin" includes, without limitation, the lips, skin of the face, hands, arms, neck, and chest. As used herein, the term "consisting essentially of" is intended to limit the invention to the specified materials or steps and those that do not materially affect the basic and novel characteristics of the claimed invention, as understood from a reading of this specification.

As used herein, the term "thymosin beta-4" refers to a protein, such as the proteins encoded in humans by the TMSB4X gene and in mice by the tmsb4x gene. The thymosin beta-4 protein (and its associated RNA and/or DNA encoding thymosin beta-4) as described in the present invention may be from any animal, but is typically human or mouse thymosin beta-4, and preferably human thymosin beta-4. The nomenclature used herein to describe specific thymosin beta-4 examples is that of the National Center for Biotechnology Information ("NCBI"), Accession Numbers NP_066932 (human, thymosin beta-4, protein), NM_021109 (human, thymosin beta-4, mRNA), NP_067253 (mouse, thymosin beta-4, protein), NM_021278 (mouse, thymosin beta-4, mRNA), which are hereby incorporated by reference and summarized in Table 1 (see SEQ ID NOs: 1-4).

Thymosin beta-4 as encompassed by the present invention includes any full-length, fragment or derivative of this protein having the biological functions of thymosin beta-4, as well as the corresponding RNA and/or DNA sequences encoding thymosin beta-4, as obtained from any animal. As used herein, thymosin beta-4 also refers to a genus of polypeptides that further encompasses proteins having the amino acid sequence of SEQ ID NO:1 and SEQ ID NO:3, as well as those proteins and polypeptides having a high degree of similarity (at least 90% homology) with such amino acid sequences and which proteins and polypeptides have the biological functions of thymosin beta-4. Additionally, the oligonucleotide comprising a part of or an entire sequence of the nucleic acid sequence described in SEQ ID NO:2 or SEQ ID NO:4 for use in the present invention includes, for example, an oligonucleotide comprising a base sequence sharing about 70% or more, preferably about 80% or more, more preferably about 90% or more, and furthermore preferably about 95% or more of homology with the nucleic acid sequence described in SEQ ID NO:2 or SEQ ID NO:4, or an oligonucleotide comprising a part of or an entire sequence of the nucleic acid sequence described in SEQ ID NO:2 or SEQ ID NO:4 of the sequence listing.

a screening method for identifying potential thymosin beta-4 stimulators. In one embodiment, an assay is provided for determining the expression levels of thymosin beta-4 after a cell has been treated, incubated, or otherwise contacted with

TABLE 1

| Gene Symbol | Sequence | Accession No. | Sequence ID No. |
|---|---|---|---|
| TMSB4X (human)-protein | msdkpdmaei ekfdksklkk tetqeknplp sketieqekq ages | NP_066932 | SEQ ID NO: 1 |
| TMSB4X (human)-mRNA | gacaactcgg tggtggccac tgcgcagacc agacttcgct cgtactcgtg cgcctcgctt cgcttttcct ccgcaaccat gtctgacaaa cccgatatgg ctgagatcga gaaattcgat aagtcgaaac tgaagaagac agagacgcaa gagaaaaatc cactgccttc caaagaaacg attgaacagg agaagcaagc aggcgaatcg taatgaggcg tgcgccgcca atatgcactg tacattccac aagcattgcc ttcttatttt acttctttta gctgtttaac tttgtaagat gcaaagaggt tggatcaagt ttaaatgact gtgctgcccc tttcacatca aagaactact gacaacgaag gccgcgcctg catttcccat ctgtctatct atctggctgg cagggaagga aagaacttgc atgttggtga aggaagaagt ggggtggaag aagtggggtg ggacgacagt gaaatctaga gtaaaaccaa gctggcccaa ggtgtcctgc aggctgtaat gcagtttaat cagagtgcca ttttttttt tgttcaaatg atttaatta ttggaatgca caatttttt aatatgcaaa taaaagttt aaaacttaa aaaaaaaaaa aaaaaaaaaa aaaaaaa | NM_021109 | SEQ ID NO: 2 |
| tmsb4x (mouse)-protein | msdkpdmaei ekfdksklkk tetqeknplp sketieqekq ages | NP_067253 | SEQ ID NO: 3 |
| tmsb4x (mouse)-mRNA | atcacctcat ttgcatagaa gcacacataa agcggcgttc gccgcgcccc tcccgacaat ccgcagcggc ttctgagcag atcagactct cctcgttcgc gcagctcgct cggctccttc cagcaaccat gtctgacaaa cccgatatgg ctgagatcga gaaattcgat aagtcgaagt tgaagaaaac agaaacgcaa gagaaaaatc ctctgccttc aaaagaaaca attgaacaag agaagcaagc tggcgaatcg taatgaggcg agcgccgcca atatgcactg tacattccac gagcattgcc ttcttatttt acttctttta gctgtttaac tttgtaagat gcaaagaggt tggatcaagt ttaaatgact gtgctgcccc tttcacatca aagaatcaga actactgagc aggaaggcct cccctgcctc tcccacccat ctgatggtct ggctagcaga gagggaaaag aacttgcatg ttggtgaagg aaaaagctgg gtgggagatg atgaaataga gaggaaaatt caagatggtc aaagatgtcc tgcaggatgt aaaatgcagt ttaatcagag tgccattttt ttttgttcaa acaattttaa ttattggaat gcacaatttt tttaatatgc aaataaagtt ttaaaacctg | NM_021278 | SEQ ID NO: 4 |

The term "stimulator" encompasses any substance, including, without limitation, organic molecules; biomolecules (e.g., peptides, proteins, antibodies, nucleic acid oligomers, etc.); and combinations of substances, such as botanical extracts. The stimulators may stimulate the cellular levels of thymosin beta-4, by which is meant that the cellular levels of thymosin beta-4 protein are increased by the active agent. The term "stimulation" may refer to upregulation, induction, stimulation, and/or potentiation, or relief of inhibition. The stimulators may also be, without limitation, activators, or agonists, which are compounds that, for example, bind to, stimulate, increase, open, activate, facilitate, enhance activation, sensitize, or upregulate expression levels of genes or thymosin beta-4 proteins or peptides. The mechanism by which the protein level is modulated is not important.

As used herein, the term "expression levels" refers to an amount of a gene and/or protein that is expressed in a cell. As used herein, a "gene" includes a polynucleotide containing at least one open reading frame that is capable of encoding a particular polypeptide. As used herein, the terms "polynucleotide" is synonymous with "oligonucleotide" and includes polymeric forms of nucleotides of any length, either deoxyribonucleotides or ribonucleotides, or analogs thereof, including, without limitation, mRNA, DNA, cDNA, primers, probes, and the like.

The discovery of the correlation between the expression levels of thymosin beta-4 and dermatological aging has led to a candidate substance. The term "candidate substance" refers to any substance that is tested for activity as a stimulator of thymosin beta-4, whether or not the substance is suspected of possessing such activity, other than retinoids. The cell can be any cell from any animal wherein the cell expresses thymosin beta-4. In one embodiment, the cell is a mammalian fibroblast. In another embodiment, the cell is a mammalian keratinocyte. Preferably, the cell is a human or mouse cell. After the cell has been incubated with a candidate substance for a sufficient length of time to provide a measurable change in expression levels, which will typically be at least one hour, and more typically from about 12 hours to about 72 hours, the cell is then lysed to release the cellular components, such as thymosin beta-4 and mRNA encoding thymosin beta-4. The amount of thymosin beta-4 protein or mRNA may then be measured by any suitable technique for detection and quantitation of peptides and proteins and/or polynucleotides (e.g., mRNA).

The preferred methods for measuring expression levels of thymosin beta-4 involve the quantitation of mRNA expression. Suitable methods for determining mRNA expression include quantitative PCR (QPCR), real-time QPCR, reverse transcription PCR (RT-PCR), and quantitative reverse transcription PCR (QRT-PCR), as are well-known in the art. As described in detail in U.S. Pat. Nos. 7,101,663 and 7,662,561, the disclosures of which are hereby incorporated by reference, a quantitative reverse transcriptase polymerase chain reaction (QRT-PCR) for detecting mRNA may include the steps of: (a) incubating an RNA sample from the cellular lysate with a reverse transcriptase and a high concentration of a target sequence-specific reverse transcriptase primer under conditions suitable to generate cDNA; (b) subsequently adding suitable polymerase chain reaction (PCR) reagents to the reverse transcriptase reaction, including a high concentration of a PCR primer set specific to the cDNA and a thermostable DNA polymerase to the reverse transcriptase reaction; and (c) cycling the PCR reaction for a desired number of cycles and under suitable conditions to generate PCR products ("amplicons") specific to the cDNA. The products of the QRT-PCR process may be compared after a fixed number of PCR cycles to determine the relative quantity of the RNA species as compared to a given reference gene, for example, GAPDH (glyceraldehyde-3-phosphate dehydrogenase). More typically, the progress of the PCR reaction is monitored by analyzing the relative rates of amplicon production for each PCR primer set, for example, by (1) non-specific fluorescent dyes that intercalate with any double-stranded DNA, and/or (2) sequence-specific DNA probes consisting of oligonucleotides that are labeled with a fluorescent reporter which permits detection only after hybridization of the probe with its complementary DNA target.

The mRNA may be any mRNA that is associated with thymosin beta-4 from any animal, including the mRNAs encoding thymosin beta-4, such as those identified in Table 1, or any polynucleotide, fragment or derivative thereof. In one embodiment, the mRNA encodes thymosin beta-4, among others. In a preferred embodiment, the mRNA encodes human thymosin beta-4.

The level of mRNA expression may be compared to controls that are not treated with the candidate substance to determine the relative degree of stimulation. In some embodiments, the candidate substance will upregulate mRNA expression by at least about 10%, more suitably at least about 20%, at least about 30%, at least about 40%, or at least about 50%. Preferably, the candidate substance will upregulate mRNA expression by at least about 60%, at least about 70%, at least about 80%, at least about 90%, or at least about 100%. Candidate substances meeting these criteria, other than retinoids, may be selected for use of for further evaluation. Retinoids, such as retinol A and retinoic acid, are the most common active agents used in anti-wrinkle creams. However, the use of retinoids on the skin has been associated with various side effects, e.g. skin irritation, redness and itching, skin peeling, dry skin, and sensitivity to sunlight.

The thymosin beta-4 stimulators of the invention, such as those identified by the foregoing screening protocol, may be used as active agents in cosmetic preparation and may be formulated with other cosmetically acceptable components, such as a vehicle, into a composition for topical application to the skin. The use of these thymosin beta-4 stimulators results in less skin irritation, redness and itching, skin peeling, dry skin, and sensitivity to sunlight compared to the use of retinoids. The compositions are topically applied to the skin in effective amounts, by which is meant an amount sufficient to achieve a measurable improvement in skin health or reduction in one or more dermatological signs of aging. Such signs of skin aging include without limitation, the following:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and/or
(r) reduction of pigment spots and/or mottled skin.

In practice, the compositions of the invention, including agents that stimulate thymosin beta-4 expression levels, alone, or in cosmetically acceptable vehicles, are applied to skin in need of treatment. That is, the compositions of the invention are applied to skin which suffers from a deficiency or loss in any of the foregoing attributes or which would otherwise benefit from improvement in any of the foregoing skin attributes. The skin is typically treated once or twice daily. The treatment may continue for a week, two weeks, four weeks, eight weeks, six months or longer. Preferably, the treatment is once daily administration for a period of at least four weeks. The length of treatment is determined by response, in particular by the effective treatment of fine lines and/or wrinkles.

In one embodiment the active agents are topically applied, in a cosmetically acceptable vehicle, to skin suffering from fine lines and/or wrinkles to prevent, treat, and/or ameliorate the appearance of the fine lines and/or wrinkles in the skin. In this case, the compositions are applied to skin in need of treatment, by which is meant skin already having wrinkles and/or fine lines or skin that is at risk of developing fine lines and/or wrinkles. Preferably, the compositions are applied directly to the fine lines and/or wrinkles on the skin of the face, neck, chest, and/or hands. Preferred agents according to this embodiment are upregulators of thymosin beta-4 expression. In a preferred embodiment, the upregulators of thymosin beta-4 expression lead to an enhanced production of collagen, estastin and/or fibrillin in dermal fibroblasts.

In one embodiment, the invention is directed to a method of improving the aesthetic appearance of skin by increasing the production of collagen, elastin, and/or fibrillin in the skin, the method comprising topically applying to an area of the skin in need thereof an effective amount of an agent that upregulates thymosin beta-4 expression, wherein said active agent has been identified for use by an assay which determines the ability of a substance to stimulate expression levels of thymosin beta-4, including the assay described herein. Preferably, the assay measures thymosin beta-4 mRNA expression levels in dermal fibroblasts.

In one embodiment, the thymosin beta-4 stimulator comprises a natural plant material such as a botanical extract. Among the natural plant materials and botanical extracts which upregulate thymosin beta-4 suitable extracts are extracts from plants selected from the following species and/or portions thereof: *Maesa japonica* (branches and leaves), *Celosia argentea* (flower), *Berchemia lineata* (whole plant), *Ixora chinesis* (flower), *Physalis minima* (whole plant), and combinations thereof.

In a preferred embodiment, the active agent, which may be a botanical extract, upregulates thymosin beta-4 in a dermal fibroblast or epidermal keratinocyte, is from *Maesa japonica*, and is combined with a topically acceptable vehicle. Optionally, the *Maesa japonica* active agent and topically acceptable vehicle are combined with a second active agent which upregulates thymosin beta-4 in a dermal fibroblast or epidermal keratinocyte.

Other active agents which upregulate thymosin beta-4 include the following compounds:

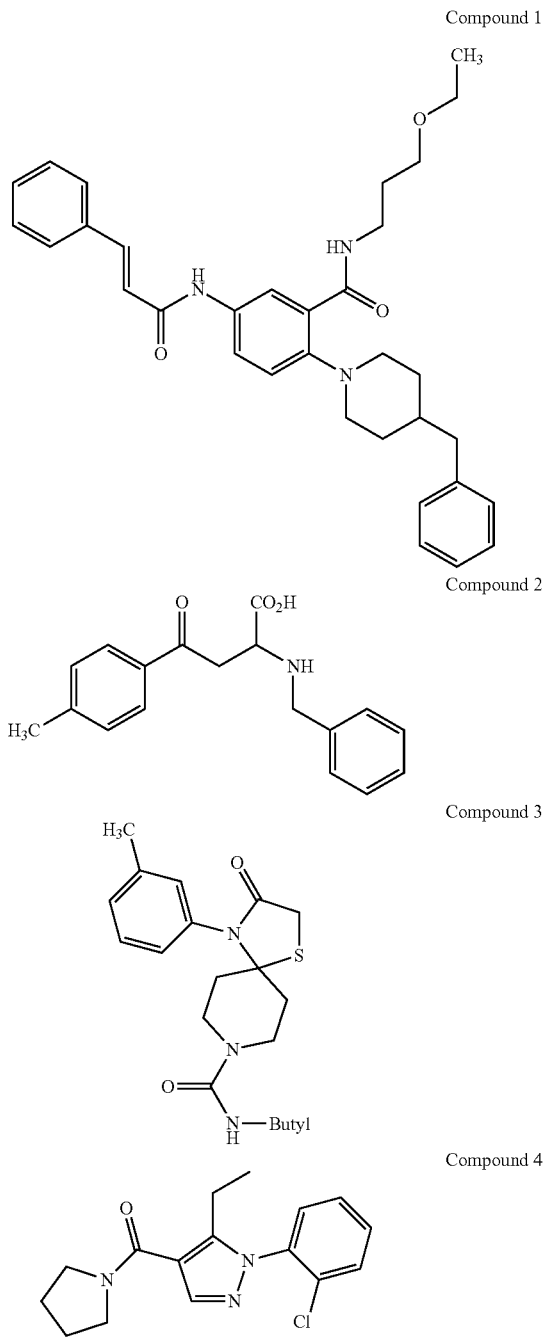

Compound 1

Compound 2

Compound 3

Compound 4

In one embodiment, the invention is directed to a cosmetic composition comprising an effective amount of Compound 1 and at least one topically acceptable vehicle. Another embodiment of the invention is directed to a method of improving the aesthetic appearance of human skin comprising topically applying to the skin in need thereof an effective amount of Compound 1 for a time sufficient to improve the aesthetic appearance of said human skin.

In one embodiment, the invention is directed to a method for improving the aesthetic appearance of human skin and/or improving the appearance of aged and/or photo-damaged skin comprises topically applying an effective amount of a composition comprising a natural plant extract from a plant selected from the group consisting of *Maesa japonica, Celosia argentea, Berchemia lineate, Ixora chinesis, Physalis minima*, or combinations thereof, and a cosmetically acceptable vehicle.

The plant materials may be in any form including, but not limited to, the whole plant, a dried plant, a ground plant, or parts thereof, including but not limited to, seeds, needles, leaves, roots, bark, cones, stems, rhizomes, callus cells, protoplasts, flowers, and meristems, or components and/or constituents found in, or isolated from, the natural plant material, and/or portions of the plant, or any combinations thereof. In one embodiment, the natural plant material is in the form of an extract derived from the whole plant or from a select portion of the plant, such as the leaves of the plant. It is to be understood that "natural plant material" also includes an ingredient, component, constituent, or extract derived from the natural plant material. In another embodiment, the plant extract as used herein, also includes "synthetic" extracts, i.e., various combinations of known plant components and/or constituents that are combined to substantially mimic the composition and/or activity of a plant extract of natural origin. Such synthetic extracts are included in the term "plant extract." The synthetic extracts will have two or more, three or more, or four or more active ingredients in common with a plant. Most preferably, the synthetic extracts will have substantially the same number of active ingredients as a natural extract. The correspondence of the numerical incidence of active ingredients between the synthetic extracts and the plant or a natural extract may also be described in terms of "percent commonality." Preferably, the synthetic extract has about 50 percent or more commonality to the chemical composition of a plant or natural extract. In other words, the synthetic extract has about 50 percent or more of the active ingredients found in the plant or a natural extract. More preferably, the chemical composition of the synthetic extract has about 70 percent or more commonality to the chemical composition of a plant or a natural extract. Optimally, a synthetic extract has about 90 percent or more commonality to the chemical composition of a plant or a natural extract.

For use in the compositions of this disclosure, the plant extract or components and/or active constituents are preferably derived directly from the plant. The components may be in a pure form, a semi-pure form, or unpurified form. In one embodiment, the components are in the form of an extract obtained by aqueous or organic solvent extraction. Non-limiting examples of organic solvents include acetic acid, diethyl ether, ethyl acetate, lower alcohols (e.g., methanol, ethanol, isopropanol, or butanol), dichloromethane, chloroform, hexane, benzene, toluene, xylene, petroleum ether, and combinations thereof. The solvent may be either polar or non-polar, protic or aprotic, water-miscible or water-immiscible. The pH may be acidic, neutral, or alkaline. Well-known methods in the art may be used for aqueous or organic solvent extraction. An extraction time between about 1-8 hours at a temperature between about 30° C. to about 90° C. is typically suitable. The collected extract is then fine-filtered to remove debris, and may be used directly, or is concentrated, for example by distilling the solvent or by other conventional processing, and the extract can also be provided in powder form.

The cosmetic compositions according to the invention can be formulated in a variety of forms for topical application and will comprise an effective amount of an active agent that modulates or upregulates thymosin beta-4, wherein the active agent or agents comprises from about 0.00001% to about 90% by weight of the composition, and preferably will comprise from about 0.001% to about 25% by weight, and more preferably from about 0.01% to about 10% by weight. The active agent may also be present from about 0.5% to about 5% by weight.

The compositions can include a cosmetically acceptable vehicle. Such vehicles may take the form of any known in the art suitable for application to skin and may include, but are not limited to, water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, hydrocarbon oils such as mineral oil, petrolatum, isoeicosane and polyisobutene; polyols such as propylene glycol, glycerin, butylene glycol, pentylene glycol and hexylene glycol; liposomes; waxes; or any combinations or mixtures of the foregoing.

The vehicle may comprise an aqueous phase, an oil phase, an alcohol, a silicone phase or mixtures thereof and may be in the form of an emulsion. Non-limiting examples of suitable emulsions include water-in-oil emulsions, oil-in-water emulsions, silicone-in-water emulsions, water-in-silicone emulsions, glycerin-in-oil emulsions, wax-in-water emulsions, water-oil-water triple emulsions or the like. The emulsion may include an emulsifier, such as a nonionic, anionic or amphoteric surfactant, or a gelling agent.

The topical composition will typically have a pH range from 1 to 8, with a pH in the range of from 2 to 7 being preferred. In some embodiment, the composition will have a pH in the range of from 3.5 to 5.5. Suitable pH adjusters such as citric acid and triethanolamine may be added to bring the pH within the desired range.

In one embodiment of the invention, the compositions may include additional skin actives, including but not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors.

The composition may comprise additional active ingredients having anti-aging benefits, as it is contemplated that synergistic improvements may be obtained with such combinations. Exemplary anti-aging components include, without limitation, botanicals (e.g., *Butea frondosa* extract); phytol; thiodipropionic acid (TDPA) and esters thereof; retinoids (e.g., 9-cis retinoic acid, 13-cis retinoic acid, all-trans retinoic acid and derivatives thereof, phytanic acid, retinol (Vitamin A) and esters thereof, such as retinol palmitate, retinol acetate and retinol propionate, and salts thereof and others); hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few. Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer; an emollient, such as isopropyl myristate, petrolatum, silicones (e.g., methicone, dimethicone), oils, mineral oils, and fatty acid esters; a humectant, such as glycerin or caprylyl glycol; a skin plumper, such as palmitoyl oligopeptide, collagen, or collagen and/or glycosaminoglycan (GAG) enhancing agents; a sunscreen, such as avobenzone; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1% by weight to about 80% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents; metal chelating agents such as EDTA; pigments; colorants; and pH adjusters. The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin disorders.

The composition may be formulated in a variety of product forms, such as, for example, an emulsion, lotion, cream, serum, spray, aerosol, cake, ointment, essence, gel, paste, patch, pencil, towelette, mask, stick, foam, elixir, concentrate, and the like, particularly for topical administration. Preferably the composition is formulated as an emulsion, lotion, cream, ointment, serum or gel.

The invention provides a method for treating aging skin by topically applying a composition comprising an active agent that stimulates thymosin beta-4, preferably in a cosmetically acceptable vehicle, over the affected area for a period of time sufficient to reduce, ameliorate, reverse or prevent dermatological signs of aging.

Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin;

reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof.

In one embodiment, the compositions will comprise from about 0.00001% to about 90%, more typically from about 0.001% to about 25%, including from about 0.01% to about 10% by weight of a stimulator of thymosin beta-4. Preferably, the stimulator may be an upregulator of thymosin beta-4 in fibroblasts. Also preferred, the stimulator may be an upregulator of thymosin beta-4 in keratinocytes. In one embodiment, the stimulator is an upregulator of thymosin beta-4 in both fibroblasts and keratinocytes. Combinations of stimulators are also contemplated. In one embodiment, the stimulator is a combination of two or more substances that are upregulators of thymosin beta-4 in fibroblasts and/or keratinocytes.

The composition will typically be applied to the skin one, two, or three times daily for as long as is necessary to achieve desired results. The treatment regiment may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). In one embodiment, the composition of the invention will be applied to the skin in an amount from about 0.001 to about 100 mg/cm$^2$, more typically from about 0.01 to about 20 mg/cm$^2$, and preferably about 0.1 to about 10 mg/cm$^2$.

It is also contemplated that the compositions of the invention will be useful for treating thin skin by topically applying the composition to thin skin of an individual in need thereof "Thin skin" is intended to include skin that is thinned due to chronological aging, menopause, or photo-damage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals.

EXAMPLES

The following examples describe specific aspects of the invention to illustrate the invention but should not be construed as limiting the invention, as the examples merely provide specific methodology useful in the understanding and practice of the invention and its various aspects.

Example 1

Thymosin Beta-4 Stimulation Assay

Normal human dermal fibroblasts were cultured in 96-well tissue culture-treated plates, containing appropriate culture medium. Stock solutions of actives were made in an appropriate vehicle (water or DMSO). Cells were treated with test material or respective vehicle control diluted in growth medium for 24 hours in a humidified 37° C. incubator with 10% $CO_2$. After incubation, growth medium from each plate was removed and 100 µL of lysis buffer was added to the wells and placed in 37° C. incubator with 10% $CO_2$ for 30 minutes. At the end of incubation, the cell lysates were collected in freezer plates and placed in −80° C. freezer until analysis. Changes in mRNA for thymosin beta-4 (TMSB4X) after treatment were analyzed using Affymetrix's QUANTIGENE® multiplex assay that employs a branched DNA signal amplification technology, following the manufacturer's instructions (Affymetrix, CA). Percent increase in mRNA for thymosin beta-4 (TMSB4X) was calculated by comparing the test results to the control. The percent up-regulation is converted to a scaled score as shown below in Table 2.

TABLE 2

| % Upregulation | Upregulation Scale |
| --- | --- |
| 0-20 | 0 |
| 21-40 | + |
| 41-60 | ++ |
| 61-80 | +++ |
| >81 | ++++ |

Example 2

Upregulation of Thymosin Beta-4

A variety of botanical extracts were tested for the ability to up-regulate Thymosin beta-4 according to the method of Example 1. The results for these active agents are provided in Table 3. The concentrations of each extract are provided based on the dry weight of the given plant extract, by which is meant the weight of the extract after volatile extraction solvents have been removed. The cells tested were primary human dermal fibroblasts.

TABLE 3

| Plant Extract | Conc. (%) | Thymosin beta-4 (TMSB4X) Degree of Upregulation |
| --- | --- | --- |
| *Maesa japonica* | 0.1 | ++++ |
| *Maesa japonica* | 0.01 | ++ |
| *Celosia argentea* | 0.01 | +++ |
| *Ixora chinesis* | 0.01 | + |
| *Physalis minima* | 0.1 | + |
| *Physalis minima* | 0.01 | + |

Synthetic compounds 1-4 were also tested as active agents for the ability to upregulate thymosin beta-4 according to the method of Example 1. The results are provided in Table 4.

TABLE 4

| Compound | Conc. (%) | Thymosin beta-4 (TMSB4X) Degree of Upregulation |
|---|---|---|
| 1 | 0.001 | ++ |
| 2 | 0.0001 | + |
| 3 | 0.0001 | + |
| 4 | 0.00001 | + |

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for cosmetically improving the aesthetic appearance of human skin comprising topically applying to an area of the human skin in need thereof a composition comprising a cosmetically a effective amount of a synthetic compound selected from the group consisting of:

Compound 1

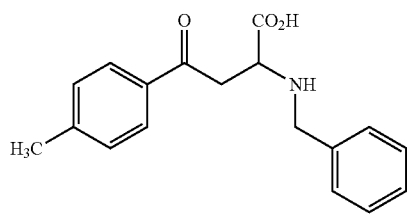

Compound 2

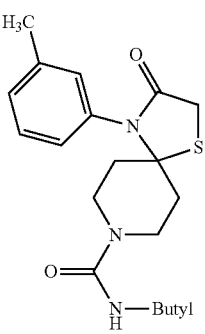

Compound 3

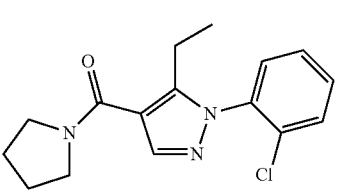

Compound 4 and combinations thereof for a time sufficient to cosmetically improve the aesthetic appearance of said human skin.

2. The method of claim 1, wherein the composition further comprises a cosmetically acceptable vehicle.

3. The method of claim 1, wherein the synthetic compound is Compound 1.

4. The method of claim 1, wherein the synthetic compound is Compound 2.

5. The method of claim 1, wherein the synthetic compound is Compound 3.

6. The method of claim 1, wherein synthetic compound is Compound 4.

* * * * *